(12) United States Patent
Meudt et al.

(10) Patent No.: US 7,022,857 B2
(45) Date of Patent: Apr. 4, 2006

(54) PREPARATION OF SUBSTITUTED AROMATIC COMPOUNDS

(75) Inventors: Andreas Meudt, Flörsheim-Weilbach (DE); Michael Erbes, Frankfurt (DE); Klaus Forstinger, Babenhausen (DE)

(73) Assignee: Clariant GmbH, Frankfurt (DE)

( * ) Notice: Subject to any disclaimer, the term of this patent is extended or adjusted under 35 U.S.C. 154(b) by 78 days.

(21) Appl. No.: 10/677,412

(22) Filed: Oct. 2, 2003

(65) Prior Publication Data

US 2004/0073032 A1 Apr. 15, 2004

Related U.S. Application Data

(62) Division of application No. 10/171,444, filed on Jun. 13, 2002, now Pat. No. 6,657,093.

(30) Foreign Application Priority Data

Jun. 20, 2001 (DE) ............................... 101 29 765
Nov. 9, 2001 (DE) ............................... 101 55 209

(51) Int. Cl.
*C07D 213/02* (2006.01)
(52) U.S. Cl. ................. 546/112; 546/139; 546/152; 546/339; 546/345; 546/348
(58) Field of Classification Search ............ 546/1, 546/339, 345, 348, 112, 139, 152
See application file for complete search history.

(56) References Cited

U.S. PATENT DOCUMENTS

| 4,398,037 | A | 8/1983 | Takeda et al. ............ 560/77 |
| 5,626,798 | A | 5/1997 | Schwindeman | |
| 6,392,047 | B1 | 5/2002 | Geissler et al. ........... 546/260 |

FOREIGN PATENT DOCUMENTS

| EP | 955291 | * 10/1999 |
| WO | WO 92 19622 | 11/1992 |

OTHER PUBLICATIONS

Hart et al., Organic Chemistry, Chapt 4.10, pp 125-126.
Guijarro, D et al., "Arene-Catalysed Lithiation of Fluoroarenes", Elsevier Sci. Pub., (Feb. 2000), vol. 56, No. 8, pp 1135-1138, Amsterdam, NL.
Beilstein On-line, Database No. 4558685 Reaction-ID XP002263418 & J. Org. Chem, vol. 61. 1996, pp 7922-7926, Frankfurt am Main, DE.
Beilstein On-line, Database No. 4691904 Reaction-ID XP002263419 & J. Org. Chem, vol. 62, 1997, pp 3315-3323, Frankfurt am Main, DE.
Beilstein On-line, Database No. 665578 Reaction-ID XP002263421 & J. Am. Chem Soc., vol. 80, 1958, pp 4976-4977, Frankfurt am Main, DE.
Beilstein On-line, Database No. 654215 Reaction-ID XP002263422 & J. Org. Chem, vol. 19. 1954, pp 817-819, Frankfurt am Main, DE.
Guijarro, A, et al., "Naphthalene-Catalysed Lithiation of Functionalized Chlorarenes", Tetrahedron, vol. 49, No. 2, 1993, pp 469-482.

* cited by examiner

*Primary Examiner*—Zinna Northington Davis
(74) *Attorney, Agent, or Firm*—Richard P. Silverman

(57) ABSTRACT

A process for preparing compounds of the formula (II),

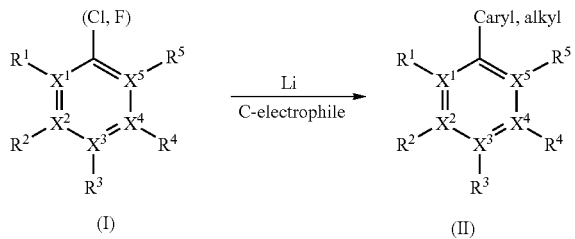

where the substituents $R^1$ to $R^5$ are each independently H, $CH_3$, straight-chain or branched $C_1$–$C_8$-alkyl, $CH(OC_1$–$C_5$-alkyl$)_2$, $CH(C_1$–$C_5$-alkyl)($OC_1$–$C_5$-alkyl), $CH_2(OC_1$–$C_5$-alkyl), $CH(CH_3)(OC_1$–$C_5$-alkyl), $C_1$–$C_8$-alkoxy, $N(C_1$–$C_5$-alkyl$)_2$, phenyl, substituted phenyl, aryl, heteroaryl, $S(C_1$–$C_5$-alkyl) or a radical $C_{aryl, alkyl}$, and
the symbols $X^{1\ to\ 5}$ are each carbon or a maximum of two neighboring $X^{1-5}$ are nitrogen or $X^1R^1$ and $X^2R^2$ together are O, NH, $N(C_1$–$C_5$-alkyl), $N(C=O—C_1$–$C_5$-alkyl)$, N(SiR_3)_2$ or S,
or where neighboring radicals $R^1$ to $R^5$ form the following structural unit,

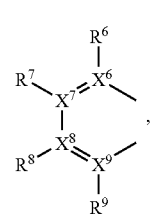

where $X^6$ to $X^9$ and $R^6$ to $R^9$ have the same meaning as $X^1$ to $X^5$ and $R^1$ to $R^5$ which comprises reacting chloro- or fluoroaromatics of the formula (I) with carbon electrophiles and lithium metal.

19 Claims, No Drawings

PREPARATION OF SUBSTITUTED AROMATIC COMPOUNDS

This application is a Divisional application of application Ser. No. 10/171,444 filed on Jun. 13, 2002, now U.S. Pat. No. 6,657,093, the contents of which is hereby incorporated by reference.

The invention relates to a process for carbon-carbon bond formation starting from chloro- or fluoroaromatics by reacting with lithium metal and a carbon electrophile, whereby a wide gamut of alkyl- or aryl-substituted aromatics and heteroaromatics may be obtained.

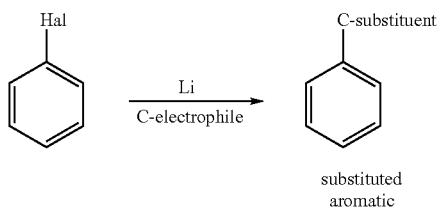

This type of conversion of chloro- and fluoroaromatics to alkyl- and aryl-substituted aromatics and heteroaromatics provides, for example, a very wide gamut of versatile intermediates and active ingredients for the agrochemical and pharmaceutical industry that are of great economic interest.

Many different routes for the conversion of haloaromatics to alkyl- or aryl-substituted aromatics are described in numerous publications, and for many of these reactions there are general procedures whereby even the target compounds in each case can be obtained in good yields.

The most important and very widely applicable general procedure is the conversion of haloaromatics to Grignard compounds, which can subsequently be reacted with a wide gamut of carbon electrophiles to give the target compounds. The reaction of bromo- or iodoaromatics to give Grignard compounds succeeds in the absence of traces in the haloaromatic which react with the Grignard functionality in almost all cases in good to very good yields. However, it must be taken into account that bromo- and iodoaromatics are almost always significantly more expensive than the corresponding chloroaromatics, so that it is obligatory to use the latter to obtain competitive industrial preparative processes. Unfortunately there are numerous cases in which, starting from the corresponding chloro- or fluoroaromatics, the Grignard compounds can only be obtained in poor yields, using specialized, often expensive solvents or using expensive activation methods for the magnesium metal. For example, this applies to 1-chloronaphthalene, which requires the use of Rieke magnesium, an example of a specialized and expensive technique, in order to achieve any worthwhile yields.

In these cases, there are hardly any alternatives to the use of the bromo- or iodoaromatics, since metallation using e.g. butyllithium does not work with chloroaromatics, and the reverse procedure, e.g. coupling of the haloaromatic with a nucleophilic reagent, such as an alkyl or aryl Grignard or a boronic acid, usually only succeeds with the more active bromo- or iodoaromatics. In the few described coupling reactions of metallates with chloro- or fluorobenzenes, it is often necessary to use large quantities of specially developed and usually very expensive ligands, so that this alternative is not usually given serious consideration.

A further significant disadvantage of the process mentioned concerns the apparatus. From the point of view of process engineering, preparing Grignard compounds from chloro- or fluoroaromatics is also problematic because the reaction frequently does not start at all at first only then to light off very suddenly and in an often uncontrolled fashion. It is often observed that the time until the start of the reaction depends very strongly on the quality of the solvent used (for example, water content, content of radical formers and metal ions, etc.). These are not ideal preconditions for a controlled industrial process.

However, the greatest problem and the biggest cost factor in the preparation of alkyl- and aryl-substituted aromatics from chloro- and fluorobenzenes is the considerable cost and effort associated with the apparatus. Since the resulting aryl metallates, for example the repeatedly mentioned aryl Grignard compounds, can only be obtained commercially in very few cases and then at horrendous cost, the Grignard compound has to be prepared in a first tank, which is usually held at reflux temperature, cooled therein after complete conversion, the appropriate carbon electrophile pre-charged to a second tank and, in view of the high reactivity of the aryl metallates, usually cooled to very low temperatures, then the similarly cooled Grignard compound metered in, thawed, hydrolyzed in a third tank (tanks 1 and 2 have to remain absolutely water-free) and the workup carried out in this third or a further tank. The simultaneous occupation of several tanks and the necessary lengthy heating and cooling phases of relatively large quantities results in only average space-time yields being achieved and high overall preparation costs.

The preparation of other organometallic reagents, e.g. based on the metals of zinc, aluminum, sodium, potassium or silicon, likewise does not present a sensible alternative, since the metals are usually too unreactive to react with chloroaromatics (Zn, Al, Si), or since the resulting metallates couple very easily to give biaryls and other products or tend to rearrange intramolecularly (K, Na, e.g. tolylsodium and tolylpotassium rearrange to give benzyl metallates).

It would therefore be very desirable to have a process—while retaining the raw materials chloro- or fluoroaromatics and carbon electrophile—which ideally involves all process steps being operated at one and the same temperature or at only slightly differing temperatures and thus avoiding long heating and cooling phases. Even more important would be the ability to carry out the preparation of the organometallic reagent in the same tank in which the reaction with the carbon electrophile is carried out. However, since the preparation of the Grignard compound usually has to be carried out at the reflux temperature of the solvent used but the addition of the reaction partner has to be carried out at temperatures of <0° C. for selectivity reasons, this does not appear to be possible via a Grignard route.

A further route which is frequently used for preparing alkyl- or aryl-substituted aromatics is the reaction of lithiated aromatics and heteroaromatics with carbon electrophiles. Lithioaromatics can likewise be prepared in numerous ways. For example, reaction of bromoaromatics and iodoaromatics with butyllithium is a standard method of generating lithioaromatics. This exchange can be carried out at low temperatures at which the reactions with carbon compounds can then be carried out with high selectivity.

However, this reaction can unfortunately not be carried out using chloroaromatics, since, with very few exceptions, these do not react with butyllithium. This fact and the high cost of butyllithium results in a process which is overall not particularly economical despite the advantages mentioned.

The prior art discloses various methods for preparing lithium compounds. However, no overall process for exchange of chlorine or fluorine with alkyl or aryl radicals which fulfills all of the requirements described above has hitherto been described.

It is an object of the present invention to provide a process for preparing compounds of the formula (I) which starts from easily available and convenient chlorine or fluorine compounds, and makes the required aryl- or alkyl-substituted aromatics and heteroaromatics accessible in good yields and high purities and is at the same time simple in process engineering terms, efficient and cost effective. The latter automatically implies the operation of all process steps with the exception of hydrolysis and workup at one and the same temperature and if possible in one and the same reaction vessel. Ideally, the process shall also make it possible to prepare the target compounds directly by simple stirring of chloroaromatic, metal and carbon electrophile in a suitable solvent.

The present invention achieves all these objects and provides a process for preparing compounds of the formula (II),

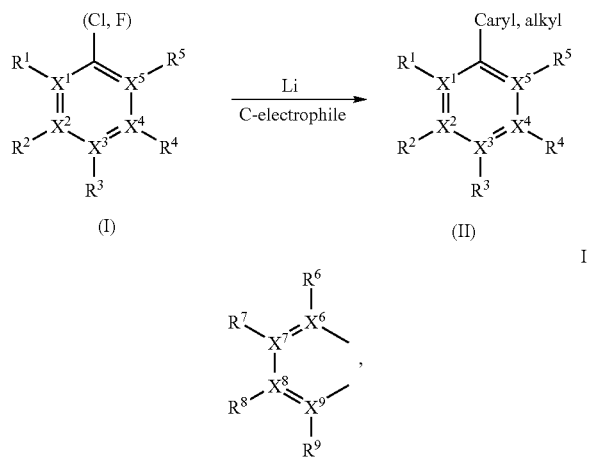

where $X^6$ to $X^9$ and $R^6$ to $R^9$ have the same meaning as $X^1$ to $X^5$ and $R^1$ to $R^5$ and the radical $C_{aryl,alkyl}$ is $CH_3$, straight-chain or branched, substituted or unsubstituted $C_1$–$C_8$-alkyl, in particular $C_1$–$C_4$-alkyl, 1-hydroxyalkyl having from 1 to 8 carbon atoms, CN, 2-hydroxyalkyl having from 2 to 5 carbon atoms, 3-hydroxyalkyl having from 3 to 5 carbon atoms, 1-NHR-alkyl having from 1 to 5 carbon atoms, $CH(OC_1$–$C_5$-alkyl$)_2$, $C(C_1$–$C_5$-alkyl)(OC$_1$–$C_5$-alkyl), $CH_2$(OC$_1$–$C_5$-alkyl), $CH(CH_3)(OC_1$–$C_5$-alkyl), $C_1$–$C_5$-alkoxy, in particular $C_1$–$C_4$-alkoxy, $N(C_1$–$C_5$-alkyl$)_2$, phenyl, substituted phenyl, aryl, heteroaryl, $CO_2H$, $CO_2$alkyl, (C=O)$_{0.5}$, (which would correspond to the structural unit Ar—CO—CO—Ar), substituted 1-vinylalkyls, $CH_3$—C(=O), R—C(=O) or CHO, which comprises reacting chloro- or fluoroaromatics of the formula (I) with carbon electrophiles and lithium metal.

The carbon electrophile is in particular selected from one of the following categories:
aryl or alkyl cyanates ($C_{aryl,alkyl}$=CN)
oxirane, substituted oxiranes ($C_{aryl,alkyl}$=$CH_2CH_2OH$, $CR_2CR_2OH$) with R=$R^1$ (identical or different)
azomethines ($C_{aryl,alkyl}$=$CR^1{}_2$—NR'H)
nitroenolates ($C_{aryl,alkyl}$=oximes)
immonium salts ($C_{aryl,alkyl}$=amines)
haloaromatics, aryl triflates, other arylsulfonates ($C_{aryl,alkyl}$=aryl, heteroaryl)
carbon dioxide ($C_{aryl,alkyl}$=COOH)
carbon monoxide ($C_{aryl,alkyl}$=(—CO—)$_{0.5}$)
aldehydes, ketones ($C_{aryl,alkyl}$=$CHR^1$—OH, $CR^1{}_2$—OH)
α,β-unsaturated aldehydes/ketones ($C_{aryl,alkyl}$=CH(OH)-vinyl, $CR^1$(OH)-vinyl)
ketenes ($C_{aryl,alkyl}$=C(=O)$CH_3$ in ketene, C(=O)—$R^1$ in substituted ketenes)
alkali metal and alkaline earth metal salts of carboxylic acids ($C_{aryl,alkyl}$=CHO in formates, $COCH_3$ in acetates, $R^1CO$ in $R^1$COOMet)
aliphatic nitriles ($C_{aryl,alkyl}$=$COCH_3$ in acetonitrile, $R^1CO$ in $R^1CN$)
aromatic nitriles ($C_{aryl,alkyl}$=COAr')
amides ($C_{aryl,alkyl}$=CHO in $HCONR_2$, C(=O)R in $RCONR'_2$)
esters ($C_{aryl,alkyl}$=[C(OH)$R^1$]$_{0.5}$) or
alkylating agents ($C_{aryl,alkyl}$=alkyl).

The process of the invention provides a method for converting the inexpensive and easily accessible chloro- and fluoroaromatics as ideal starting molecules into a wide gamut of compounds while adding value.

A preferred embodiment is the simultaneous stirring of the carbon electrophile, chloro- or fluoroaromatic and lithium metal in a suitable solvent (one-pot variant), in which, after appropriate workup (usually hydrolysis), the resulting products are often obtained in good yields. As long as no functional groups are present in the reactants which react even faster with lithium metal, the method delivers very high space-time yields and additionally only requires a single tank. In some cases, space-time yields of up to 0.3 kg of product/(L*h) are achieved.

A further preferred embodiment is particularly advantageous when, for the above or other reasons, the one-pot variant cannot be employed, and involves the primary quantitative preparation of lithium compound and subsequent reaction with carbon electrophile. In a particularly preferred embodiment, both steps are carried out at the same or only slightly differing temperatures, which allows time-consuming and energy-intensive heating and cooling phases to be avoided.

Useful solvents for the carbon-carbon bond forming method of the invention are aliphatic and aromatic ethers and hydrocarbons and amines which do not carry a hydrogen on the nitrogen atom, preferably triethylamine, diethyl ether, tetrahydrofuran, toluene, toluene/THF mixtures, anisole and diisopropyl ether, more preferably toluene, THF or diisopropyl ether. Concentrations of solutions are preferably in the range from 1 to 60% by weight, in particular 5 to 40% by weight, more preferably 8 to 30% by weight.

The conversions of the invention are advantageously carried out at temperatures in the range from −100° C. to +80° C., preferably from −80° C. to +20° C., more preferably from −65° C. to −5° C.

The lithium can be used in the present process in the form of a dispersion, a powder, turnings, sand, granules, pieces, bars or in another form, although the size of lithium particles is not qualitatively relevant, but merely influences the reaction times. For this reason, preference is given to relatively small particle sizes, for example granules, powder or dispersions. The added lithium quantity per mole of halogen to be converted is from 1.95 to 2.5 mol, preferably from 1.98 to 2.15 mol.

The workup is generally aqueous, and either water or aqueous mineral acids are metered in or the reaction mixture is metered into water or aqueous mineral acids. To achieve the best yields, the pH is set to that of the product to be isolated in each case, thus usually a slightly acidic, or in the case of N-heterocycles, slightly alkaline pH. The alkylated or arylated products are recovered, for example, by extraction and evaporation of the organic phases, or alternatively, the organic solvents may be distilled out of the hydrolysis mixture and the precipitated product recovered by filtration.

The purities of the products from the process of the invention are generally high, but for special applications (pharmaceutical precursors) a further purification step, for example by recrystallization with the use of small quantities of activated carbon, may be necessary. The yields of the reaction products are from 70 to 99%, typical yields are in particular from 85 to 95%.

The raw materials for the synthesis of the invention (chloroaromatics and fluoroaromatics) are generally commercially obtainable and very inexpensive, so that in combination with the stated process engineering advantages and associated high space-time yields and very high product purities, an extremley economical and very generally applicable process for carbon-carbon bond formation of the invention has been found.

The process of the invention is illustrated by the following nonlimiting examples:

EXAMPLES 1 TO 7

Preparation of p-methylacetophenone from Chlorotoluene

A mixture of 126.5 g (1 mol) of p-chlorotoluene and 45.1 g (1.1 mol) of acetonitrile (freshly distilled) is added dropwise to a suspension of 13.8 g (2.0 mol) of lithium granules in 350 ml of THF at −50° C. over the course of 2 hours. After a conversion determined by GC (the dark color of the reaction mixture prevents quantification of lithium consumption) of >98% (overall 7.5 h), the reaction mixture is added to 200 g of water, the pH adjusted to 2.0 using 37% HCl and the reaction mixture boiled for two hours under reflux. The organic phase is then separated off and the aqueous phase extracted once more with 100 ml of petroleum ether. The united organic phases are distilled. 132.7 g (0.99 mol) of 4-methylacetophenone (99%, boiling point 88° C./8 Torr) are obtained as a colorless liquid, GC purity >98% a/a, which when left to stand at RT gradually solidifies.

|  | Solvent | Temperature | Reaction time | % conversation of metallation |
|---|---|---|---|---|
| Example 1 | THF | −50° C. | 7.5 h | 98.5 |
| Example 2 | THF | −60° C. | 10 h | 98.3 |
| Example 3 | THF/toluene 1:1 | −40° C. | 12 h | 95.5 |
| Example 4 | THF (half quantity) | −50° C. | 7.5 h | 96.8 |
| Example 5 | Di-n-butyl ether | −35° C. | 14 h | 97.2 |
| Example 6 | Diethyl ether | −25° C. | 9 h | 98.3 |
| Example 7 | Triethylamine | −65° C. | 2 h | 98.2 |

EXAMPLE 8

Preparation of p-methylacetophenone from Fluorotoluene

The preparation of p-methylacetophenone from p-fluorotoluene was carried out as described in Example 1, except that the reaction time to the required conversion has to be doubled. The hydrolysis was carried out in a Teflon flask (HF). In this way, 4-methylacetophenone is obtained in a yield of 88%.

EXAMPLE 9

Preparation of 2-(4-isopropylphenyl)propene from 4-chloroisopropylbenzene 154.5 g (1 mol) of 4-chloroisopropylbenzene are added dropwise over the course of 1 hour to a suspension of 13.8 g (2.0 mol) of lithium granules in 400 ml of THF at −45° C. After a conversion determined by GC of >97% (overall 9.5 h), the reaction mixture is added dropwise over 30 minutes to a solution of 60.9 g (1.05 mol) of dry acetone in 120 ml of THF at −45° C. and stirred for a further 1 h at this temperature.

The reaction mixture is hydrolyzed as described in Example 1 (150 ml of water, adjust the pH to 1.0 using HCl). In order to completely eliminate water, the mixture is boiled for 6 h under reflux. The phases are then separated at room temperature and the aqueous phase extracted once more with 100 ml of petroleum ether. The united organic phases are dried over sodium sulfate and freed of remaining solvents by distillation. 152 g (0.95 mol) of 2-(4-isopropylphenyl)propene. (95%) remain as yellowish oil, GC purity 94.5% ala.

EXAMPLE 10

Preparation of 2-(4-isopropylphenyl)propene from 4-fluoroisopropylbenzene

Example 3 is repeated, except that the lithiation time must again be doubled. Yield 95%, GC purity 93.1% a/a.

EXAMPLE 11

Preparation of 4-octylbenzaldehyde from the Ethylene Glycol Acetal of 4-chlorobenzaldehyde 184.5 g (1 mol) of ethylene glycol acetal of 4-chlorobenzaldehyde are added dropwise over 2 h to a suspension of 13.8 g (2.0 mol) of lithium granules in 800 ml of THF at −50° C. After a conversion determined by GC of >97% (overall 8.5 h), 193 g (1.1 mol) of n-octyl bromide are added dropwise at −50° C. over 60 minutes and the stirring is continued for 1 h at this temperature.

After hydrolysis (220 ml of water, adjust the pH to 2.0 using HCl) and boiling for 2 h under reflux (to cleave the acetal), the organic phase is separated off and the aqueous phase extracted once more with 100 ml of petroleum ether. The united organic phases are dried over sodium sulfate and then freed from remaining solvents by distillation. 198.4 g (0.91 mol) of 4-octylbenzaldehyde (91%) remain as a pale brownish oil, GC purity 98% a/a.

EXAMPLE 12

Preparation of 4-(2-hydroxyethyl)phenetol from 4-chlorophenetole 50 g (1.14 mol) of ethylene oxide are condensed into 400 ml of THF cooled to −60° C. 13.8 g (2.0 mol) of lithium powder are then added under a nitrogen atmosphere, then 156.5 g of 4-chlorophenetole are added 10 minutes later. After attainment of a conversion determined by GC of >96% (overall 5.5 h), the reaction mixture is hydrolyzed as described in Example 1 (150 ml of water, adjust the pH to 4.0 using HCl). The phases are then separated at room temperature and the aqueous phase extracted once more with 100 ml of dichloromethane. The united organic phases are freed of remaining solvents and water by distillation. 152.7 g (0.92 mol) of 4-(2-hydroxyethyl)phenetol (92%) remain as a highly viscous liquid.

EXAMPLE 13

Preparation of 4-cyanobiphenyl 13.8 g (2.0 mol) of lithium powder are suspended in 225 ml of THF under a nitrogen atmosphere. A solution of 188.5 g of 4-chlorobiphenyl and 119 g of phenyl isocyanate in 225 ml of THF is added dropwise at −65° C. over the course of an hour. After attainment of a conversion determined by HPLC of >95% (overall 8.5 h), the reaction mixture is hydrolyzed as described in Example 1 (150 ml of water; in order to remove the by-produced phenol, the pH is left at 12.4). The phases are then separated at room temperature and the aqueous phase extracted once more with 100 ml of dichloromethane. The united organic phases are washed once more with 3% NaOH and then freed of remaining solvents and water traces by distillation. 166.5 g (0.93 mol) of 4-cyanobiphenyl (93%) remain as a colorless solid, which may, if necessary, be recrystallized from ethanol.

EXAMPLE 14

Preparation of 4-hydroxymethyl-N,N-dimethylaniline from 4-chloro-N,N-dimethylaniline 155.5 g of 4-chloro-N,N-dimethylaniline are metered into a suspension of 13.8 g (2.0 mol) of lithium powder in 400 ml of toluene cooled to −50° C. over 60 minutes. After attainment of a conversion determined by GC of >98% (overall 6.5 h), gaseous formaldehyde is bubbled into the reaction mixture until 33 g in total have been taken up. After stirring for a further 30 minutes, hydrolysis is carried out in the described manner (200 ml of water, adjust the pH to 7.0 using HCl). The phases are then separated at room temperature and the aqueous phase extracted twice more with 100 ml of dichloromethane each time. The united organic phases are freed of remaining solvents and water by distillation. 134.5 g (0.89 mol) of 4-hydroxymethyl-N,N-dimethylaniline (89%) remain as a viscous, brownish liquid.

EXAMPLE 15

Preparation of Acetophenone Oxime 112.5 g of chlorobenzene are metered into a suspension of 13.8 g (2.0 mol) of lithium powder in 400 ml of THF cooled to −50° C. over 60 minutes. After attainment of a conversion determined by GC of >99% (overall 8.5 h), the greenish reaction mixture is metered into a suspension of an enolate with nitroethane in THF (preparation: 1 mol of nitroethane, 1 mol of n-BuLi in hexane and 300 ml of THF at −50° C.). After stirring for a further 30 minutes, hydrolysis is carried out in the described manner (200 ml of water, carefully adjust to pH 6.0 using HCl). The phases are then separated at room temperature and the aqueous phase extracted once more with 100 ml of dichloromethane. The united organic phases are freed of remaining solvents and water by distillation. 101 g (0.75 mol) of acetophenone oxime (75%) remain as yellowish, highly viscous oil.

EXAMPLE 16

Preparation of 1,2-bis(4-methylthiophenyl)ethanedione 158.5 g of 4-chlorothioanisole are metered into a suspension of 13.8 g (2.0 mol) of lithium powder in 400 ml of THF cooled to −70° C. over 60 minutes. After attainment of a conversion determined by GC of >96% (overall 7.5 h), a vigorous flow of carbon monoxide is bubbled into the reddish reaction mixture at −75° C. When no more is taken up, hydrolysis is carried out in the described manner (200 ml of water, carefully adjust to pH 6.5 using HCl). The phases are then separated at room temperature and the aqueous phase extracted twice more with 100 ml of dichloromethane each time. The united organic phases are freed of remaining solvents and water by very gentle distillation. After crystallization from ethanol (96%), 83 g (0.275 mol) of 1,2-bis(4-methylthiophenyl)ethanedione (55%) remain as a brown, unpleasantly smelling solid.

EXAMPLE 17

Preparation of bis(p-anisyl)carbinol 158.5 g (1.0 mol) of 4-chlorothioanisole are metered into a suspension of 13.8 g (2.0 mol) of lithium pieces (1 cm×1 cm×0.5 cm) in 370 ml of THF cooled to 40° C. over 30 minutes. After attainment of a conversion determined by GC of >97% (overall 14.5 h), a solution of 58.8 g (0.98 mol) of methyl formate in the same volume of THF is added dropwise into the reaction mixture at −40° C. After stirring at −40° C. for a further hour, hydrolysis is carried out in the repeatedly described manner (200 ml of water, adjust to pH 6.5 using HCl). The phases are then separated at room temperature and the aqueous phase extracted a further three times with 100 ml of dichloromethane each time. The united organic phases are freed of remaining solvents and water by distillation. 108.6 g (0.445 mol) of bis(p-anisyl)carbinol (89%) remain as a yellowish viscous product.

EXAMPLE 18

Preparation of 4-methoxybiphenyl 142.5 g (1.0 mol) of 4-chloroanisole are metered into a suspension of 13.8 g (2.0 mol) of lithium lumps (1 cm×1 cm×0.5 cm) in 370 ml of THF cooled to −50° C. over 50 minutes. After attainment of a conversion determined by GC of >97% (overall 12.5 h), a solution of 0.05 g of $PdCl_2$ (dppf) in 20 ml of THF is first added dropwise to the reaction mixture at −50° C. and then a solution of 157 g of bromobenzene in the same volume of THF is added dropwise over 30 minutes (strongly exothermic). After stirring at −50° C. for a further hour, the mixture is allowed to warm to room temperature and hydrolyzed in the described manner (200 ml of water, adjust the pH to 5.5 using HCl). The phases are then separated at room temperature and the aqueous phase extracted once more with 150 ml of toluene. The united organic phases are freed of remaining solvents and water by distillation. 162 g (0.88 mol) of 4-methoxybiphenyl (88%) remain as a slightly yellowish solid, which may be purified further by distillation.

|  | Solvent | Temperature | Reaction time | % Yield |
| --- | --- | --- | --- | --- |
| Example 8 | THF | −50° C. | 15 h | 88 |
| Example 9 | THF | −45° C. | 9.5 h | 95 |
| Example 10 | THF/toluene 1:1 | −40° C. | 24 h | 93.1 |
| Example 11 | THF | −50° C. | 8.5 h | 91 |
| Example 12 | THF | −60° C. | 5.5 h | 92 |
| Example 13 | THF | −65° C. | 8.5 h | 93 |
| Example 14 | Toluene | −50° C. | 6.5 h | 89 |
| Example 15 | THF | −50° C. | 8.5 h | 75 |
| Example 16 | THF | −70° C. | 7.5 h | 96 |
| Example 17 | THF | −40° C. | 14.5 h | 89 |
| Example 18 | THF | −50° C. | 12.5 h | 88 |

EXAMPLE 19

Preparation of 3-acetylpyridine from 3-chloropyridine

A mixture of 113.5 g (1 mol) of 3-chloropyridine and 45.1 g (1.1 mol) of acetonitrile (freshly distilled) is added dropwise to a suspension of 13.8 g (2.0 mol) of lithium granules in 350 ml of THF at −75° C. over 2 hours. After attainment of a conversion determined by GC of >95% (overall 17.5 h), the reaction mixture is worked up in the repeatedly described manner. After filtration of the remaining toluenic solution through Primisil high-density zeolite and the condensing of the solvent, 110 g of 3-acetylpyridine (HPLC purity 93%) remain as an orange liquid.

EXAMPLE 20

Preparation of 3-acetylfuran from 3-chlorofuran

Example 19 is repeated, except that the reactants are 102.5 g (1 mol) of 3-chlorofuran, 45.1 g (1.1 mol) of acetonitrile (freshly distilled) and 13.8 g (2.0 mol) of lithium granules. 98.5 g of 3-acetylfuran (HPLC purity 94%) are obtained as a light brown liquid.

What is claimed is:

1. A process for preparing compounds of the formula (II),

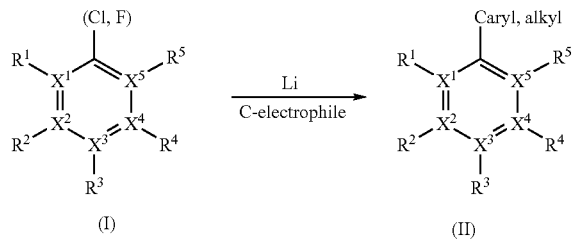

where the substituents $R^1$ to $R^5$ are each independently H, $CH_3$, straight-chain or branched $C_1$–$C_8$-alkyl, $CH(OC_1$–$C_6$-alkyl$)_2$, $CH(C_1$–$C_5$-alkyl)(OC_1$–$C_5$-alkyl), $CH_2(OC_1$–$C_5$-alkyl), $CH(CH_3)(OC_1$–$C_5$-alkyl), $C_1$–$C_8$-alkoxy, $N(C_1$–$C_5$-alkyl$)_2$, phenyl, substituted phenyl, aryl, heteroaryl, $S(C_1$–$C_5$-alkyl) or a radical $C_{aryl, alkyl}$, and the symbols $X^{1\ to\ 5}$ are each carbon with at least one $X^{1-5}$ being nitrogen or with at least one $X^{1-5}$ being nitrogen and $X^1R^1$ and $X^2R^2$ together are O, NH, $N(C_1$–$C_5$-alkyl), $N(C=O-C_1$–$C_5$-alkyl), $N(SiR_3)_2$ or S, or where neighboring radicals $R_1$ to $R_5$ form the following structural unit,

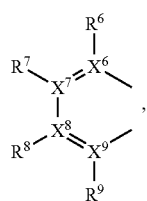

I where $X^6$ to $X^9$ and $R^6$ to $R^9$ have the same meaning as $X^1$ to $X^5$ and $R^1$ to $R^5$ and the radical $C_{aryl,\ alkyl}$ is straight-chain or branched, substituted or unsubstituted $C_1$–$C_8$-alkyl, 1-hydroxyalkyl having from 1 to 8 carbon atoms, CN, 2-hydroxyalkyl having from 2 to 5 carbon atoms, 3-hydroxyalkyl having from 3 to 5 carbon atoms, 1-NHR-, $CH(OC_1$–$C_5$-alkyl$)_2$, $C(C_1$–$C_5$-alkyl)(OC_1$–$C_5$-alkyl), $CH_2(OC_1$–$C_5$-alkyl), $CH(CH_3)(OC_1$–$C_5$-alkyl), $C_1$–$C_5$-alkoxy, $N(C_1$–$C_5$-alkyl$)_2$, phenyl, substituted phenyl, aryl, heteroaryl, $CO_2H$, $CO_2$alkyl, $(C=O)_{0.5}$, substituted 1-vinylalkyls, $CH_3$—$C(=O)$, R—$C(=O)$ or CHO, wherein R is an alkyl having from 1 to 5 carbon atoms, which comprises reacting chloro- or fluoroaromatics of the formula (I) with carbon electrophiles and lithium metal.

2. The process as claimed in claim 1, wherein the carbon electrophile is selected from the group consisting of:
   aryl or alkyl cyanates ($C_{aryl,alkyl}$=CN)
   oxirane, substituted oxiranes ($C_{aryl,alkyl}$=$CH_2CH_2OH$, substituted $CR_2CR_2OH$)
   azomethines ($C_{aryl,alkyl}$=$CR^1{}_2$—$NR^1H$)
   nitroenolates ($C_{aryl,alkyl}$=oximes)
   immonium salts ($C_{aryl,alkyl}$=amines)
   haloaromatics, aryl triflates, other arylsulfonates ($C_{aryl,alkyl}$=aryl, heteroaryl)
   carbon dioxide ($C_{aryl,alkyl}$=COOH)
   carbon monoxide ($C_{aryl,alkyl}$=(—CO—$)_{0.5}$)
   aldehydes, ketones ($C_{aryl,alkyl}$+$CHR^1$—OH, $CR^1{}_2$—OH)
   α,β-unsaturated aldehydes/ketones ($C_{aryl,alkyl}$=CH(OH)-vinyl, $CR^1$(OH)-vinyl)
   ketenes ($C_{aryl,alkyl}$=C(=O)$CH_3$ in ketene, C(=O)—R, wherein R is an alkyl having from 1 to 5 carbon atoms in substituted ketenes)
   alkali metal and alkaline earth metal salts of carboxylic acids ($C_{aryl,alkyl}$=CHO in formates, $COCH_3$ in acetates, $R^1CO$ in $R^1COOCH_3$)
   aliphatic nitriles ($C_{aryl,alkyl}$=$COCH_3$ in acetonitrile, $R^1CO$ in $R^1CN$)
   aromatic nitriles ($C_{aryl,alkyl}$=COAr⁻)
   amides ($C_{aryl,alkyl}$=CHO in $HCONR^1{}_2$, $C(=O)R^1$ in $R^1CONR^1{}_2$)
   esters ($C_{aryl,alkyl}$=$[C(OH)R^1]_{0.5}$),
   alkylating agents ($C_{aryl,alkyl}$=alkyl), and mixtures thereof.

3. The process as claimed in claim 1, wherein the reaction is performed at a temperature in the range from −100 to +80° C.

4. The process as claimed in claim 1, wherein lithium is used in the form of a dispersion, powder, turnings, sand, granules, pieces or in the form of bars.

5. The process as claimed in claim 1, wherein the solvent used is an aliphatic or aromatic ether, a hydrocarbon or an amine which does not carry a hydrogen on the nitrogen atom, selected from the group consisting of triethylamine, diethyl ether, tetrahydrofuran, toluene, toluene-THF mixtures, anisole, diisopropyl ether, and mixtures thereof.

6. The process as claimed in claim 1, wherein the process is performed as a one-pot process.

7. The process as claimed in claim 1, wherein the organolithium compound is first generated and then reacted with the carbon electrophile at the same or a slightly different temperature.

8. The process as claimed in claim 2, wherein the reaction is performed at a temperature in the range from −100 to +80° C.

9. The process as claimed in claim 2, wherein lithium is used in the form of a dispersion, powder, turnings, sand, granules, pieces or in the form of bars.

10. The process as claimed in claim 2, wherein the solvent used is an aliphatic or aromatic ether, a hydrocarbon or an amine which does not carry a hydrogen on the nitrogen atom, selected from the group consisting of triethylamine, diethyl ether, tetrahydrofuran, toluene, toluene-THF mixtures, anisole, diisopropyl ether, and mixtures thereof.

11. The process as claimed in claim 2, wherein the process is performed as a one-pot process.

12. The process as claimed in claim 2, wherein the organolithium compound is first generated and then reacted with the carbon electrophile at the same or a slightly different temperature.

13. The process as claimed in claim 3, wherein lithium is used in the form of a dispersion, powder, turnings, sand, granules, pieces or in the form of bars.

14. The process as claimed in claim 3, wherein the solvent used is an aliphatic or aromatic ether, a hydrocarbon or an amine which does not carry a hydrogen on the nitrogen atom, selected from the group consisting of triethylamine, diethyl ether, tetrahydrofuran, toluene, toluene-THF mixtures, anisole, diisopropyl ether, and mixtures thereof.

15. The process as claimed in claim 3, wherein the process is performed as a one-pot process.

16. The process as claimed in claim 3, wherein the organolithium compound is first generated and then reacted with the carbon electrophile at the same or a slightly different temperature.

17. The process as claimed in claim 4, wherein the solvent used is an aliphatic or aromatic ether, a hydrocarbon or an amine which does not carry a hydrogen on the nitrogen atom, selected from the group consisting of triethylamine, diethyl ether, tetrahydrofuran, toluene, toluene-THF mixtures, anisole, diisopropyl ether, and mixtures thereof.

18. The process as claimed in claim 4, wherein the process is performed as a one-pot process.

19. The process as claimed in claim 4, wherein the organolithium compound is first generated and then reacted with the carbon electrophile at the same or a slightly different temperature.

* * * * *